United States Patent [19]

Nashef

[11] Patent Number: 4,894,063
[45] Date of Patent: Jan. 16, 1990

[54] BARRIER LAYER FOR IMPLANTABLE TENDONS AND LIGAMENTS

[75] Inventor: Aws S. Nashef, Costa Mesa, Calif.

[73] Assignee: Baxter International Inc., Deerfield, Ill.

[21] Appl. No.: 497,490

[22] Filed: May 24, 1983

[51] Int. Cl.$^4$ ................................................ A61F 2/08
[52] U.S. Cl. ........................................ 623/13; 613/18; 613/66
[58] Field of Search .................. 3/1, 1.4, 1.5, 1.9; 128/92 C, 334 R

[56] References Cited

U.S. PATENT DOCUMENTS

| | | | |
|---|---|---|---|
| 3,988,782 | 11/1976 | Dandile et al. | 3/1.4 |
| 4,400,833 | 8/1983 | Dollode et al. | 3/1 |
| 4,402,697 | 9/1983 | Kurland | 3/1 |
| 4,467,478 | 8/1984 | Jurgutis | 3/1 |

Primary Examiner—Richard J. Apley
Assistant Examiner—David J. Isabella
Attorney, Agent, or Firm—Bernard, Rothwell & Brown

[57] ABSTRACT

Disclosed is a method of interfacing a ligament substitute within a channel of resected bone with a sleeve of soft biological tissue. The sleeve of tissue has overall external dimension sufficient to extend through at least a portion of the resected bone channel and internal dimensions sufficient to receive a ligament substitute therein.

30 Claims, 1 Drawing Sheet

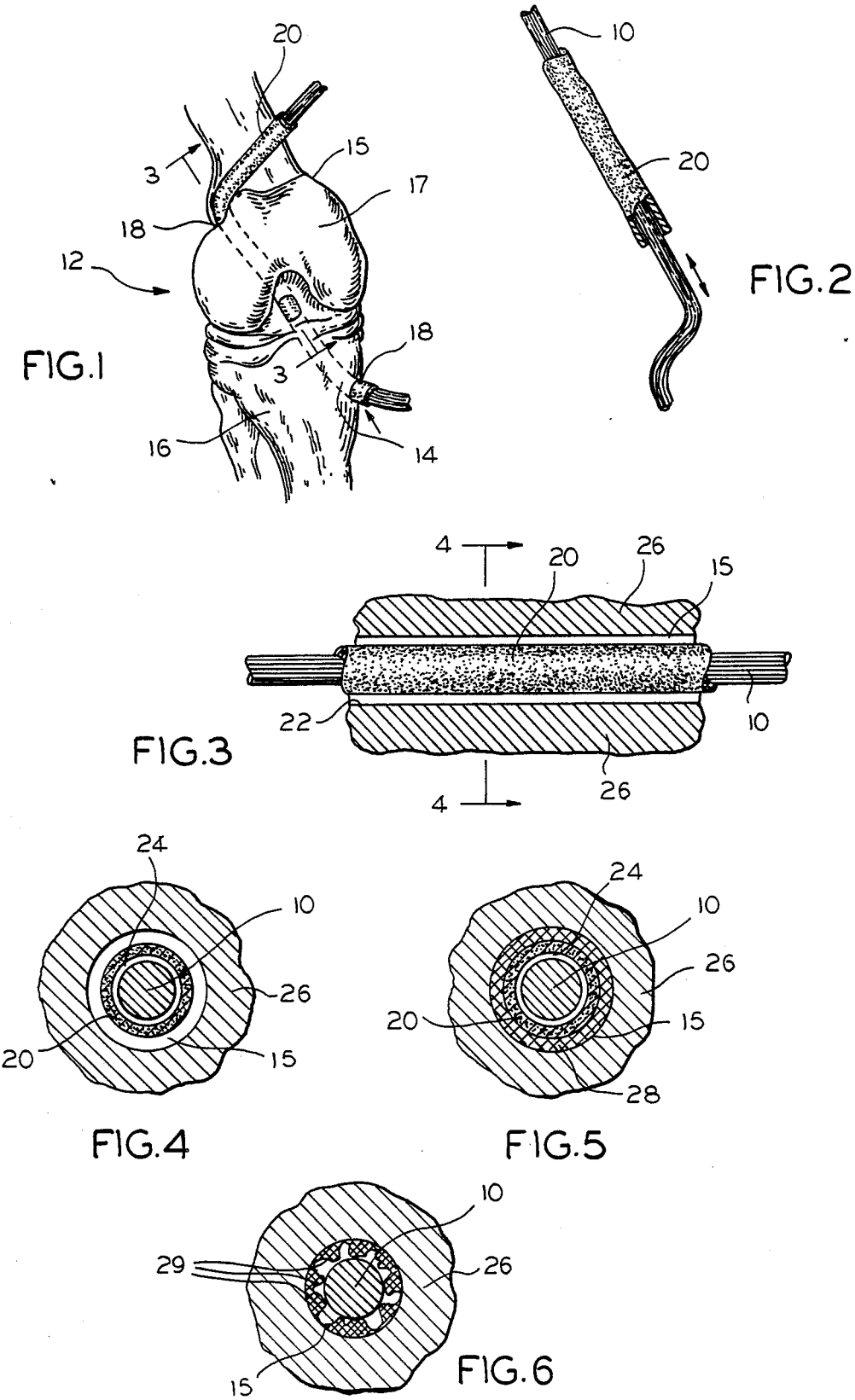

BARRIER LAYER FOR IMPLANTABLE TENDONS AND LIGAMENTS

BACKGROUND OF THE INVENTION

Injury to weight-bearing ligaments such as the cruciate ligaments of the knee can occur, either as an isolated injury, or in combination with other ligament injuries of the knee. Damaged or torn cruciate ligaments can be repaired, reconstructed or treated nonoperatively depending upon the extent of the injury, the amount of functional or clinical laxity, the age of the patient, and the activity level desired. Simple repair of the injured ligament involves suturing, and because the cruciate ligaments are poorly vascularized, simple repair is generally insufficient. Reconstruction generally involves the utilization of synthetic ligament substitutes or autologous tissue within the knee joint similar to the cruciate ligament, such as in intraarticular reconstruction, or utilization of autologous tissue outside of the knee joint to strengthen the anterior or anterior lateral rotational stability, such as in extraarticular reconstruction.

Intraarticular reconstruction of anterior and posterior cruciate ligaments of the knee generally involves drilling holes through the tibia and femur followed by insertion of a ligament substitute such as patellar tendon, fascia, and the like through the central channel, and stapling of the ligament substitute to the outer surface of the bone adjacent the resected channel. The most common mode of failure is generally observed at the place where the ligament is subjected to stress; at the site where the ligament substitute enters or exits from the tibia or femur. Ordinarily the bone grows around and into the implanted ligament during the healing process leaving high stress concentrations at these exit sites. Moreover, the ingrowth of resected bone into the ligament implant throughout the length of the resected bone channel, which immobilizes the implant by restricting its naturally intended gliding motion and reducing its flexibility, may damage the implant due to sharp, jagged, irregular bone edges formed during the healing process.

Various attempts to improve the durability, compatibility, and mechanical functioning of naturally occurring and prosthetic tendons and ligaments have only been marginally successful. Such remedies include covering the ligament substitute with a vitreous carbon coating; plastic sheaths made of polyethylene, silicone rubber, and the like; silicone rubber-reinforced Dacron mesh sleeves; woven meshes of synthetic plastic fibers; stainless steel sleeves; metal wire meshes; and the like. Heretofore, implantable ligament substitutes in close proximity with resected bone have suffered the effects of irregular bone formation, high stress levels, and marginal durability.

SUMMARY OF THE INVENTION

In accordance with the present invention, disclosed is a method of interfacing a tendon or ligament within a channel of resected bone, comprising inserting a substantially cylindrical sleeve of soft biological tissue through a channel of resected bone such that a barrier is formed between said resected bone and a tendon or ligament inserted therethrough, said sleeve having a first and second open end portion, and a longitudinal passage extending between said first and second end portions, wherein said longitudinal passage has internal dimensions sufficient to receive a tendon or ligament therethrough, and overall external dimensions sufficient to extend through at least a portion of the resected bone channel. A surgical implant kit is disclosed for use in the present invention.

DESCRIPTION OF THE DRAWINGS

FIG. 1 is a front elevational view of a human knee having a cruciate ligament substitute implanted therein in accordance with the present invention;

FIG. 2 is an isolated view, partially cut away, of a ligament substitute sliding within the sleeve of the present invention;

FIG. 3 is a sectional view of the ligament and sleeve within the resected bone channel of the femur, taken along line 3—3 of FIG. 1;

FIG. 4 is a cross-sectional view of the ligament and sleeve within the resected bone channel of the femur, taken along line 4—4 of of FIG. 3;

FIG. 5 is a cross-sectional view similar to that of FIG. 4, showing the regular new bone growth between the surface of the resected bone channel and the sleeve of the present invention;

FIG. 6 is a cross-sectional view similar to that of FIGS. 4 and 5, showing the irregular new bone growth between the surface of the resected bone channel and the implanted ligament substitute without the benefit of the present invention.

DETAILED DESCRIPTION OF THE PRESENT INVENTION

In accordance with the present invention, disclosed is a substantially cylindrical sleeve for interfacing between surgically implantable tendon or ligaments and the interior surface of resected bone channels. By way of example, the sleeve may be inserted into the tibia and femur of a mammal for anterior and posterior cruciate ligament intraarticular reconstruction of the knee. The sleeve advantageously protects the implanted tendon or other suitable ligament substitute from damage caused by the growth of sharp, irregular edges on the resected bone surface; provides a moist environment of extracellular fluid around the implant and thus increases both its flexibility and durability; promotes relatively smooth remodeling or reshaping of the resected bone surface into a regular edge; and lowers stretching (stress levels) throughout the channel in the healing process since a larger portion of the full length of the implant may become available for shouldering strain, and consequently permits easier early motion of the knee after surgery.

For the purpose of illustrating the present invention, a cruciate ligament substitute 10 implanted through the tibia and femur of the knee 12 is shown in FIG. 1. The ligament substitute is implanted in the knee 12 by drilling channels 14 and 15 through the tibia 16 and femur 17 respectively as shown in the drawing. The implant is shown having its truncated ends extending outwardly from the resected bone channel edge 18, however, it is to be understood that these ends are conventionally secured to the tibia 16 and femur 17 by stapling, and the like during the reconstructive surgery, which coes not constitute part of the present invention and will not be further described hereinafter.

In our illustration of intraarticular reconstruction, the cruciate ligament is normally replaced with autologous tissue used as fascialata, patellar tendon, semimembranous tendon, or synthetic ligaments such as polypropylene, proplast, Dacron, carbon fiber, polyethylene, and Teflon composites. In the broadest aspects of the present invention, the term implantable ligament substitute describes any synthetic or naturally occurring material which can be used to replace ligaments in the human body. These include, but are not limited to naturally occurring tendons and ligaments, biolgial tissue, or synthetic tendons and ligaments. Preferably, the ligament substitute will have from about 165 to about 390 pounds of tensile pull strength six months after surgery. The ligament substitute in accordance with one embodiment of the present invention is a glutaraldehyde-fixed bovine-bifurcated extensor tendon, and one which has preferably been treated prior to implantation with one of several available methods to reduce the calcification thereof after implantation. The sleeve of biological tissue in accordance with the present invention advantageously interfaces between resected bone and synthetic implants, which do not have the same properties as the fixed biological tissue of naturally occurring ligaments and tendons.

In accordance with the present invention, a sheath or sleeve 20 is inserted into the resected bone channel 15 in order to interface between the resected bone surface 22 and the implanted ligament or tendon 10 such that a barrier is formed therebetween as shown in FIGS. 3 and 4. The external dimensions of the sleeve 20 will vary depending upon the length and cross-sectional area of the channel within the bone 26. In one embodiment of the present invention, the sleeve has a length sufficient to extend through at least a portion of the resected bone channel 15, and preferably is positioned at the external edge 18 of the channel. In an alternate embodiment of the present invention, the length of the sleeve 20 is sufficient to cover a major portion of the channel, and more preferably the entire interior surface of the resected bone channel is covered by the sleeve. In a preferred embodiment of the present invention, the sleeve has a length which is sufficient to cover the entire interior surface 22 of the resected bone channel and which is sufficient to extend beyond the edge 18 a short distance as shown by the arrow in FIG. 1. The portion of the sleeve 20 extending beyond this edge 18 is preferably flared outwardly. The cross-sectional area of the sleeve 20 is such that the outer surface of the sleeve will be in close proximity to the interior surface 22 of the resected channel, and preferably the outer surface of the sleeve has substantially the same diameter as that of the channel interior. The embodiment shown in the drawings shows a distance which is slightly exaggerated for ease of illustration. The sleeve 20 is preferably substantially cylindrical in shape so that it will conform to the interior of the channel, and resembles a tube having open ends and a longitudinal passage 24 extending therebetween. The internal dimensions of the sleeve are sufficient to receive a tendon or ligament substitute therethrough. By way of example, the preferred bovine-bifurcated extension tendon of the present invention is approximately 230 mm long, 8 mm wide, and 4 mm thick.

Alternately, the biological tissue may be relatively short and be shaped to fit into the ends of the resected channel 18 only and to extend outwardly around the entrance to the channel such that the ligament substitute will be covered by the tissue at the point it contacts the bone edge 18 and along the side of the bone adjacent the resected channel.

In accordance with the present invention, the sleeve 20 is made of soft biological tissue such as naturally occuring biolgial tissue derived from various animal sources including but not limited to bovine, porcine, horse, sheep, kangaroo, or rabbit; and can be obtained from various parts of the anatomy as described hereinbelow. Alternatively, the biological tissue can be composed of collagen or reconstituted collagen substitutes including but not limited to collagen-fabric films, collagen-membranes, reconstituted collagen on Dacron mesh, tanned collagen sponge grafts and the like. In accordance with the present invention, the soft biological tissue cushions the implant and provides a moist, lubricious, and flexible interface between the bone and implant; and also promotes the even, remodeling of resected bone resulting in a smooth bone surface. It is understood that soft biological tissue differs from hard biological tissue found in bone, teeth, and the like.

In accordance with the present invention, naturally occurring biological tissue is removed from its host, defatted if necessary and processed in one of several well-known procedures used to prepare the tissue for implantation into humans. The tissue is fixed (tanned) conventionally in from about 0.2 to about 0.6 weight percent glutaraldehyde in either phosphate-buffered solutions, or phosphate-free buffers as described in the copending U.S. patent application Ser. No. 445,345 filed on Nov. 29, 1982. The tissue handling conditions, as conventionally known, are not considered part of the present invention unless otherwise stated. Likewise, tissue may be sterilized conventionally in about 0.625 percent glutaraldehyde or from about 4 to about 5 percent formaldehyde.

Naturally occuring biological tissue in accordance with the present invention icludes, but is not limited to epithelial and fibrous connective tissue such as pericardial tissue, dura mater, fascialata, amnion, tendon, ligament, and the like. Veins and arteries already shaped in a sleeve-like structure are also useful in the present invention. The epithelial tissues such as dura mater, amnion, facialata, and percardium generally comprise two layers each; a fibrous, proteinaceous layer and a relatively smooth membranous layer. In accordance with a preferred embodiment of the present invention, the rough, fibrous layer of the tissue is placed against the resected bone to provide better anchoring to the bone surface, while the smooth, membranous layer is directed toward the ligament substitute to provide a more lubricious passageway. In accordance with the present invention, pericardial tissue which has its edges sewn together to form an elongated tube-like structure is the preferred sleeve.

In accordance with the most preferred embodiment of the present invention, the natural biological tissue is treated prior to implantation to render it substantially resistant to calcification. This advantageously maintains the biological tissue in a more flexible state than calcified tissue, allowing the tissue to conform better to the uneven surface of the resected bone, and provides a softer surface to the resected bone prompting better bone healing. Moreover, the calcification-resistant sleeve will ultimately reduce the calcium deposits in the interior passage 24 of the sleeve 20 where the ligament substitute must be able to move freely as shown in FIG. 2. Calcification mitigation treatments of biological tissue are not considered part of the present invention but can be found in copending U.S. patent applications Ser. Nos. 445,345 filed Nov. 29, 1982; 377,747 filed May 13, 1982; and 441,023 filed Nov. 12, 1982; and in U.S. Pat. No. 4,323,358.

In accodance with the present invention, we have found significant differences in the formation of new surfaces on resected bone when using sleeves of glutaraldehyde-fixed biological tissue inserted into the drilled holes of the tibia and femur than when no such sleeves are used. First, we drilled holes having a diameter of 0.172 inches in the tibia and femur of a rabbit adjacent the knee and observed that the resected bone randomly throughout the interior of the resected channel. Secondly, and in a separately drilled hole, we inserted a glutaraldehyde-fixed tendon through the tibia and femur of a rabbit knee and observed that the resected bone grew around the periphery of the channel in a somewhat irregular pattern as illustrated in FIG. 6 at 29. We repeated this experiment, but this time used a glutaraldehyde-fixed tendon which had been treated prior to implantation to render the tendon substantially resistant to calcification. We observed similarly-formed irregular bone growth about the periphery of the channel; however, the tendon did not calcify within passageway 24 and was not visible by X-rays. Finally, we formed a sleeve of glutaraldehyde-fixed pericardial tissue by sewing the tissue into a tube-like structure having an external diameter the same as the bone channel interior with the fibrous layer on the exterior surface, and inserted this sleeve into the bone channel. Substantially uniform bone growth around the periphery of the channel was observed, resulting in a substantially cylindrical channel free of jagged bone edges within the resected bone as illustrated at 28 in FIG. 5. The sleeve of biological tissue not only contained the bone growth between the exterior of the sleeve and the interior surface of the resected bone channel, but more importantly it promoted the smooth, even, remodeling of the bone 28 at this interface.

In accordance with the present invention, the surgically-implantable sleeve 20 is sold in a sterile package or in combination with a suitable ligament substitute in a surgical implant kit capable of being used in conjunction with the repair or replacement of damaged ligaments. This kit advantageously permits the physician to assemble the sleeve 20 and ligament substitute 10 in the operating theatre by first inserting the properly-dimensioned sleeve into the resected bone channel 14 and 15 of the tibia and femur and then inserting a correspondingly dimensioned ligament substitute 10 therethrough. Alternately, the ligament substitute may be inserted through the sleeve prior to inserting both within the resected channel as shown in FIG. 2.

The present invention has been described in detail and with specific reference to its preferred embodiments, however, it will be understood by those skilled in the art that modifications can be made thereto without departing from the spirit and scope thereof.

I claim:

1. A method of interfacing a tendon or ligament within a channel of resected bone, comprising: inserting a substantially cylindrical sleeve having an outer surface of soft biological tissue through a channel of resected bone such that the biological tissue is in contact with said resected bone and a barrier is formed between said resected bone and a tendon or ligament inserted therethrough; said sleeve having a first and second open end portion, a longitudinal passage extending between said first and second end portions, wherein said longitudinal passage has internal dimensions sufficient to receive a tendon or ligament therethrough, and overall external dimensions sufficient to extend through at least a portion of the resected bone channel.

2. The method of claim 1 wherein the sleeve is naturally occurring biological tissue fixed with glutaraldehyde.

3. The method of claim 2 wherein the biological tissue is epithelial or fibrous connective tissue.

4. The method of claim 2 wherein the biological tissue is selected from the group consisting of pericardial tissue, dura mater, fascialata, or amnion.

5. The method of claim 2 wherein the biological tissue is a vein or an artery.

6. The method of claim 2 wherein the tissue is substantially resistant to calcification.

7. The method of claim 6 wherein the sleeve is made of pericardial tissue sewn together in a tube-like structure having its fibrous surface on the exterior of the sleeve.

8. The method of claim 1 wherein the sleeve is inserted into the ends of said channel such that the interior surface of the resected bone at the external edge portion is covered by said sleeve.

9. The method of claim 1 wherein the sleeve has a length sufficient to cover the entire interior surface of the resected bone channel.

10. The method of claim 9 wherein the sleeve has a length sufficient to extend beyond the edge of said resected bone channel.

11. The method of claim 10 wherein the sleeve is naturally occurring biological tissue fixed with glutaraldehyde.

12. The method of claim 11 wherein the biological tissue is epithelial or fibrous connective tissue.

13. The method of claim 11 wherein the biological tissue is selected from the group consisting of pericardial tissue, dura mater, fascilialata, or amnion.

14. The method of claim 11 wherein the biological tissue is a vein or an artery.

15. The method of claim 11 wherein the biological tissue is substantially resistant to calcification.

16. The method of claim 15 wherein the sleeve is made of pericardial tissue sewn together in a tube-like structure having its fibrous surface on the exterior of the sleeve.

17. A substantially cylindrical sleeve of soft biological tissue having a first and second open end portion, a longitudinal passage extending between said first and second end portions, wherein said longitudinal passage has internal dimensions sufficient to receive a tendon or ligament there through, and a length sufficient both to cover the entire interior surface of a resected bone channel, and to extend beyond the edge of said resected bone channel, such that said sleeve can be inserted through a channel of resected bone in accordance with claim 10, wherein the first and second end portions of the sleeve are outwardly flared.

18. The sleeve of claim 17 wherein the tissue is naturally occurring biological tissue fixed with glutaraldehyde.

19. The sleeve of claim 18 wherein the biological tissue is epithelial or fibrous connective tissue.

20. The sleeve of claim 19 wherein the biological tissue is selected from the group consisting of pericardial tissue, dura mater, fascilialata, or amnion.

21. The sleeve of claim 19 wherein the biological tissue is a vein or an artery.

22. The sleeve of claim 19 wherein the biological tissue is substantially resistant to calcification.

23. The sleeve of claim 22 wherein the sleeve is made of pericardial tissue sewn together in a tube-like structure having its fibrous surface on the exterior of the sleeve.

24. A surgical implant kit having component parts capable of being assembled in the operating theatre for repairing or replacing tendons or ligaments, wherein said tendons or ligaments are in close proximity to resected bone, the kit comprising the combination of:
- a prosthetic or naturally occurring tendon or ligament adapted to be affixed to the resected bone; and
- a substantially cylindrical sleeve having an outer surface of soft biological tissue such that the biological tissue is in contact with said resected bone when implanted; said sleeve having a first and second open end portion, a longitudinal passage extending between said first and second portions, wherein said longitudinal passage has internal dimensions sufficient to receive a tendon or ligament therethrough; and external dimensions sufficient to extend through at least a portion of the resected bone channel;
- such that said biological tissue provides a barrier to said tendon or ligament from irregular edges of said resected bone.

25. The surgical kit of claim 24 wherein the sleeve is naturally occuring biological tissue fixed with glutaraldehyde.

26. The surgical kit of claim 25 wherein the biological tissue is epithelial or fibrous connective tissue.

27. The surgical kit of claim 25 wherein the sleeve is made of pericardial tissue sewn together in a tube-like structure having its fibrous surface on the exterior surface of the sleeve.

28. The surgical kit of claim 24 wherein the biological tissue is substantially resistant to calcification.

29. The surgical kit of claim 24 wherein the naturally occurring tendon or ligament is fixed with glutaraldehyde.

30. The surgical kit of claim 24 wherein the tendon or ligament is a synthetic prosthesis.

* * * * *